United States Patent [19]
Schwabe

[11] 4,149,556
[45] Apr. 17, 1979

[54] TUBULAR CONNECTOR HAVING AUDIBLE RELIEF VALVE

[75] Inventor: Robert D. Schwabe, Morton Grove, Ill.

[73] Assignee: Respiratory Care, Inc., Arlington Heights, Ill.

[21] Appl. No.: 945,863

[22] Filed: Sep. 26, 1978

[51] Int. Cl.² ............... F16K 37/00; F17D 3/01; A61M 15/00; B01F 3/04

[52] U.S. Cl. ............... 137/115; 128/186; 128/194; 137/853; 261/78 A; 261/121 R; 261/DIG. 65

[58] Field of Search ............... 261/78 A, 63, 122–124, 261/121 R, DIG. 65; 128/186–194; 239/338, 370; 137/557, 843, 852, 853, 854, 859, 860, 115; 425/524

[56] References Cited

U.S. PATENT DOCUMENTS

| | | | |
|---|---|---|---|
| Re. 27,155 | 7/1971 | Hansen | 425/524 |
| 2,709,577 | 5/1955 | Pohndorf et al. | 239/338 X |
| 3,376,884 | 4/1968 | Bucknell et al. | 137/852 X |
| 3,527,242 | 9/1970 | Ansite | 137/852 X |
| 3,807,445 | 4/1974 | McPhee | 137/843 X |
| 3,807,713 | 4/1974 | Cornett et al. | 261/122 |
| 3,852,385 | 12/1974 | Huggins | 128/188 X |
| 3,913,843 | 10/1975 | Cambio, Jr. | 261/78 A X |
| 4,045,525 | 8/1977 | Huggins | 261/124 |
| 4,051,847 | 10/1977 | Henkin | 128/188 X |
| 4,061,698 | 12/1977 | Thornwald | 261/DIG. 65 |

Primary Examiner—Richard L. Chiesa
Attorney, Agent, or Firm—Eric P. Schellin

[57] ABSTRACT

There is disclosed a tubular connector for connecting the end of a tubular gas carrying conduit to the mouth of a thermoplastic bottle containing a liquid wherein the mouth prior to use has a breachable seal. The connector comprises two oppositely facing cup means each having internal threads therein, one to be screwed to the gas conduit the other to the mouth of the bottle. The two so disposed cups are connected by axially disposed tubular means extending respectively from each bottom of the cups whereby they are maintained in spaced relationship. That cup that is attached to a gas conduit is supplied with a relief valve at the bottom of the cup whereby excess gas pressure in the system is permitted to escape. At the same time a thin annular membrane is associated with the said relief valve whereby an audible sound is achieved due to the escaping gas.

7 Claims, 5 Drawing Figures

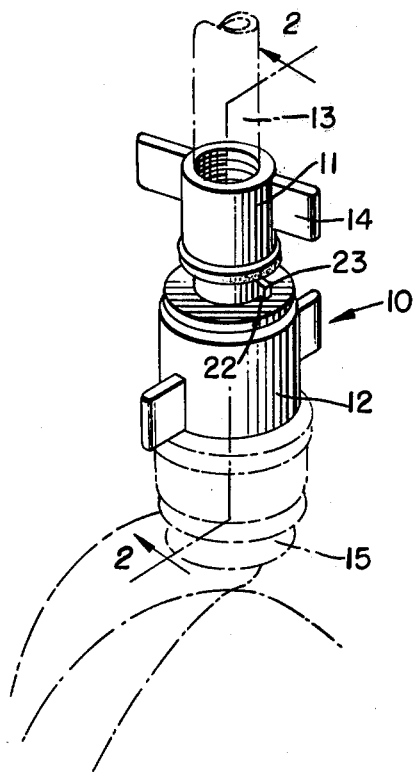
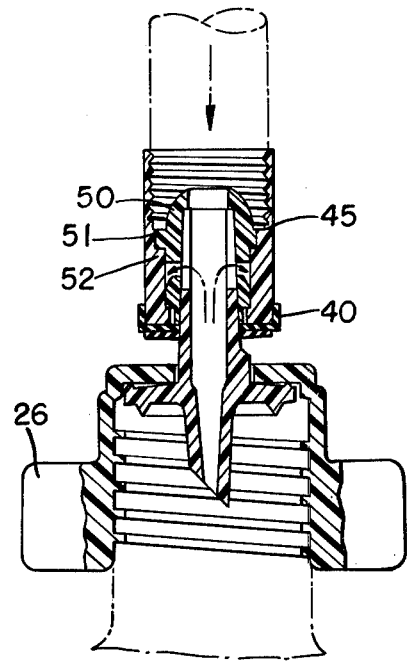
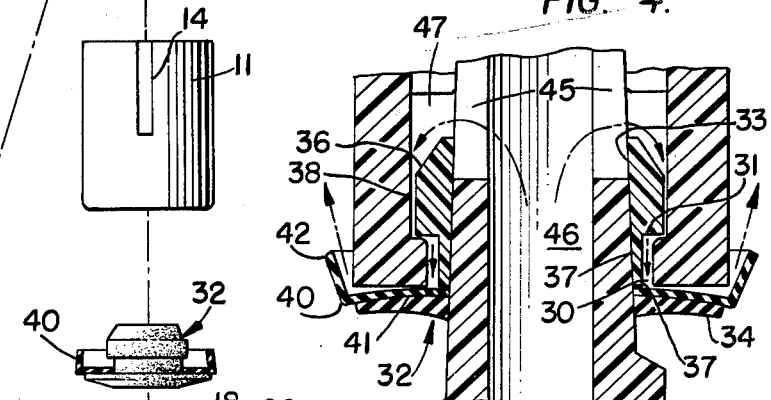
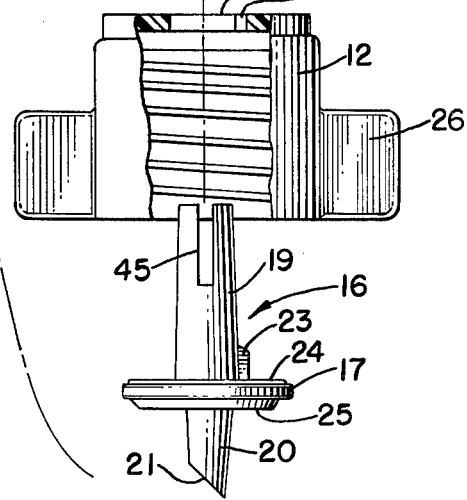

TUBULAR CONNECTOR HAVING AUDIBLE RELIEF VALVE

BACKGROUND OF THE INVENTION

The present matter deals with connectors found in regard to humidification of gas such as air or oxygen prior to delivery to a patient. Considerable activity of late has resulted in numerous inventions for delivery of humidified air or gas to patients. In supplying water it has been found efficacious to supply the water from prefilled sterile thermoplastic bottles wherein the bottle is blow molded and prior to closing of the bottle is filled with water. Reissue U.S. Pat. No. 27,155 discloses the basic concept of such a practice.

In order to make for practical use of such blown and prefilled bottles for the purpose intended, particular configurations of the bottle have been set forth with adapted connecting means of the type shown in U.S. Pat. No. 3,807,713.

It has been discovered that the delivery system may sometimes be occluded or pressure delivery may be too great, resulting in higher than desired pressures in the system. To provide for relief of such excess pressures various prior art techniques have been noted, some of which include an audible means to alert hospital attendants when gas is in fact being dumped.

For instance McPhee in U.S. Pat. No. 3,807,445 discloses an audible pressure relief valve in a medical humidifier. It is located in separate by-pass. A diaphragm is employed which is a resilient disc.

Henkin in U.S. Pat. No. 4,051,847 discloses an anesthesia breathing apparatus where a resilient disc diaphragm is used.

Huggins in U.S. Pat. No. 3,852,385 discloses in a gas humidification apparatus for delivery to a patient wherein an umbrella shaped relief valve is disposed in the outlet side of the humidifier adapter.

Cambio, Jr. in U.S. Pat. No. 3,913,843 discloses an audible relief valve in the adapter of a humidifier unit. However the relief valve is a duck bill type and is located in the housing body of the active device.

Huggins in U.S. Pat. No. 4,045,525 discloses a gas humidification apparatus wherein a relief valve is positioned downstream from the humidification means itself. However, it is of interest as being a relief valve which covers the circumference of a tube carrying the humidified gases. The valve is said to be a resilient band which merely covers a relief hole in the outlet tube.

SUMMARY OF THE INVENTION

The present invention is to a connector means of known construction wherein two connector cups are secured in oppositely facing directions. They are connected by a tubular means which extends into and through the bottom of each respective cup. One cup is attached to a plastic bottle having a breachable membrane seal so that the tubular means terminates in a penetrating spike in that cup. The other cup is attached to the terminus of a gas carrying conduit. This cup is fitted with means for carrying excess pressure presented by the gas through suitably disposed ports in that part of the tubular means in this cup. The gas is then permitted to escape through the bottom of the cup, through an annularly disposed relief valve is located about the tubular means and externally with respect to the cup. The relief valve is fitted with an annular means of soft rubber which has an upwardly extending skirt adapted to normally hug the bottom corner edge portion of the connector and the excess pressure gas flow is between this edge portion and the annular means. As the gas flow occurs, the skirt vibrates to give an audible signal.

BRIEF DESCRIPTION OF THE DRAWINGS

FIG. 1 is a perspective view of the connector of the present invention depicted as being affixed to a bottle shown in fragmentary form and by dotted lines.

FIG. 2 is a cross-sectional view of one embodiment of the connector of the present invention taken along line 2—2 of FIG. 1.

FIG. 3 is an exploded view of the connector of the embodiment of FIG. 2 with a portion of one part partly broken away.

FIG. 4 is an enlarged cross-section view of a part of the embodiment of FIG. 2 depicting the operation of the device to produce an audible signal.

DETAILED DESCRIPTION OF THE EMBODIMENTS OF THE INVENTION

Figure 5:
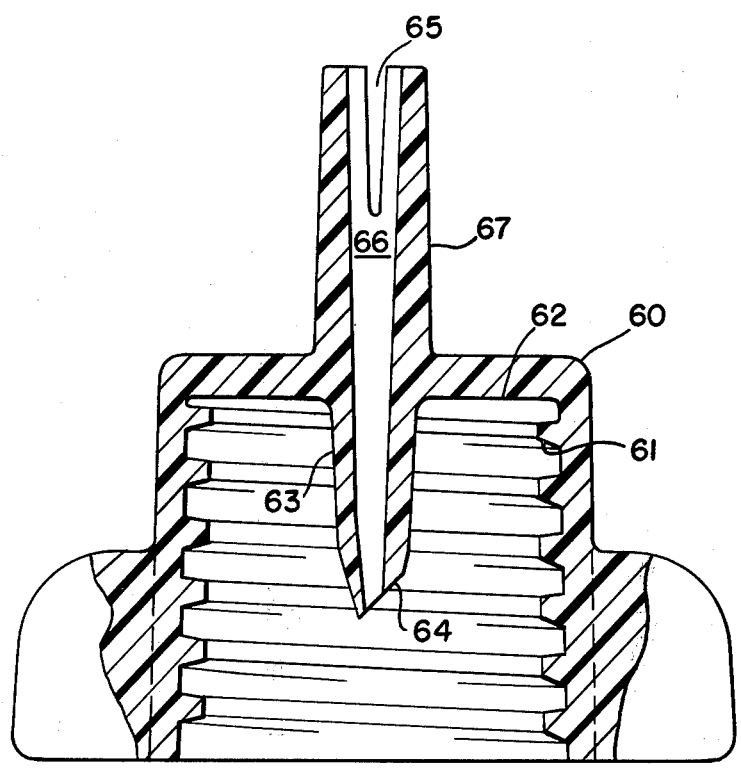
FIG. 5 is a cross-sectional view of another embodiment of the bottle connector means.

Attention is now directed to the drawings and especially FIG. 1 for a perspective view of the connector assembly 10 of the present invention. It will be noted that there is depicted an upper female cup connector 11 and a lower female cup connector 12 of somewhat larger dimension. The upper connector 11 is attached to a gas carrying conduit 13 shown by dotted lines. The end of the conduit 13 possesses a thread male member adapted and constructed to mate internally of the upper connector 11 as shown. Externally of the upper connector, two ears 14 are provided to assist in the rotation of the upper connector to effect the desired connection.

There below is the lower connector 12 which is illustrated as being connected to the mouth of a thermoplastic bottle 15, a portion of the neck portion is illustrated. The mouth of the bottle is normally closed with a breachable membrane seal, not shown, externally of the mouth is a male threaded portion onto which the connector 12 is screwed in a conventional manner. Provision is provided, as will be further discussed below, to breach the aforementioned breachable seal so that there may be direct communication with the contents and/or space in the main body portion of the bottle through its neck.

From the drawings it will be noted that tubular connecting means 16 is adapted and constructed to communicatively connect the upper cup connector with the lower cup connector and thereby the gas carrying conduit 13 with the inside of the bottle. The tubular connecting means has a radially extending flange 17 intermediate the ends thereof which is designed to be positioned internally of said lower connector. The latter has an opening 18 through which tubular portion 19 passes whereby upper surface 24 of the flange 17 may sealingly rest against the bottom of the lower cup connector. Tubular portion 19 has a slight frusto-conical configuration. At the other side of the flange 17 is downwardly extending tubular portion 20, having a more pronounced conical configuration and terminating in a bevel 21 to thereby provide a spike adapted to penetrate the breachable seal of the bottle when the lower connector cup is screwed onto the bottle. Opening 18 is provided with a plurality of axial slots 22, one of which is shown in FIG. 1, for instance. These slots are designed to act as axial key ways for small radially extending protruberances 23 so that as lower cup connector is rotated the tubular connecting means 16 may also be rotated or not rotated as desired to effect the penetration. When the tubular connecting means 16 rests loosely into the lower connector cup the protruberances being of fairly short axial longitudinal dimension permits the said cup to freely rotate until the upwardly facing portion of the mouth of the bottle comes in contact with the downwardly facing portion 25 of the flange 17, that with further rotation of the lower cup connector drives the tubular connecting means 16 whereby upper surface of flange 24 rests against the bottom of the lower cup connector. It will be noted that the lower cup connector is also fitted with ears 26 to assist in grasping the said lower cup connector.

The upper connector cup also has a passageway 30 in the bottom thereof. The passageway 30 is supplied with a plurality of axial disposed spaced slots 31 therearound. The tubular portion 19 extends through the passageway 30, the outer wall of which is spaced from the slotted walls of the passageway. The passageway is fitted with an umbrella valve 32 which has a bore 33 therethrough of a dimension whereby tubular portion 19 is snugly fitted. The bottom of the valve 32 has a thin radially extending annular flange 34, of approximately the same diameter as the outer diameter of the upper cup connector. The upper portion of the valve has a thickened portion 36 to provide greater valve retention means. The flange and the thickened portion has a relatively thin cylindrical tubular connecting portion 37, the outer circumference of which is in abutment with the bridging portions between the slots in the aforementioned passageway. It will be noted that the outer diameter of the thickened portion is slightly less than the inner diameter of the upper cup connector whereby an annual passageway 38 is provided through which higher pressure gas may be dissipated.

Prior to assembly of the device of the present invention annular audible cup 40 is positioned on the umbrella valve 32. The audible cup 40 possesses an annular flat portion 41 having an outer diameter slightly larger than the outer diameter of the bottom of the upper cup connector. The annular flat portion 41 has an upwardly extending skirt 42 with an internal diameter of a dimension whereby it fits quite snugly against the outer surface of the upper cup connector. The audible cup 40 has a centrally disposed opening which is of a diameter to conveniently fit about cylindrical tubular connecting portion 37. By constructing the audible cup of a highly elastomeric material such as thin natural rubber, the said cup may be easily stretched over the said thickened portion and snapped into place.

The upper part of tubular portoion 19 of the tubular connecting means 16 possesses passage slots 45 so that there is intercommunication between the bore 46 of the tubular connecting means 16 and the annular space 47 present in the upper cup connector. More about the need for this feature will be supplied hereinafter.

In order to complete the assembly of the device of the present invention an annular seal cap 50 is adhesively connected to the upper terminating part of the tubular portion 19. The cap has a shoulder 51 which sealingly abuts against a complementary shoulder 52 internally of the upper cap connector. It also possesses a rounded upwardly facing surface whereby the end portion of the gas carrying conduit 13 when threaded into the upper cup connector presses axially against the seal cap 50 to provide a leak proof seal in a conventional manner.

In operation, after the appropriate gas connections have been achieved and the device has been suitably connected to a bottle of water as mentioned, gas, such as oxygen is introduced under pressure. As long as the system for down stream delivery has not been occluded, the system functions to deliver humidified gas to a patient. In the event there is a pressure build up due to an occluded line or due to unwarranted increase in the pressure of the gas being delivered to the system, the device of the present invention has not only a built in pressure relief means but also accomplishes such relief with an audible signal.

For the particulars of the operation of the system, attention is directed to FIG. 4. Note that in the event of excess pressure build up in bore 46 which is, of course, in communication with the system, the gas flowingly escapes through passage slots 45 and into annular space 47, thence through annular passageway 38, then through slots 31. The gas pressure build up carries gas between the upwardly facing bottom of audible cup 40 and the downwardly facing bottom of the upper cup connector and in so doing concomitantly deflects the flange 34 of the umbrella valve, as demonstrated by the FIG. 4. The excess pressurized gas then flows between the skirt 42 and the outer cylindrical surface of the upper cup connector in a pulsatile or resonant manner whereby the audible cup, especially the skirt thereof, vibrates in a sufficiently rapid manner to provide an audible alarm to inform those within hearing of an occlusion in the delivery system so that it may be corrected.

It will be appreciated that the device of the present invention may be constructed of one of a number of applicable materials. As the assembly may be disposable, it has been found efficacious to construct the assembly of thermosetting and/or thermoplastic materials. The more rigidity required the more likelihood of the use of thermosetting plastics. Of course the umbrella valve should be constructed of flexible resilient material so should be constructed of natural rubber, synthetic rubber or some plastic having appropriate properties. The audible cup has already been considered as being constructed of rubber so that it can relatively easily vibrate in a reed-like manner.

In another embodiment of the present invention it has been found useful in the more economical assembly of the device of the present invention to provide for the integral combination of the tubular portion 19 with the integration thereof with the lower cup connector. Accordingly, attention is directed to FIG. 5 which depicts it for the same purpose as hereinbefore described. Note that lower cup connector 60 is similar as before, having an inner female threaded portion 61 and a bottom 62. The inside of the bottom has a concentrically disposed spike 63 with a bevel 64 for the purpose of penetrating a breachable seal of a thermoplastic bottle. Externally of the bottom 62 is an outwardly concentrically extending tubular portion 67 of a slightly frusto-conical configuration having slots 65 at the upper portion thereof. A bore 66 axially through the spike and the tubular portion. The thusly modified lower cup connector is assembled to the same type of upper cup connector as heretofore as discussed in the above.

What is claimed is:

1. A gas connector having an audible relief valve comprising:

(a) an upper cup means adapted and constructed to be connected to a pressurized gas carrying conduit means;

(b) a lower cup means adapted and constructed to be connected to the mouth of a liquid carrying receptacle;

(c) a tubular connecting means interconnecting the bottom of the lower cup means to the bottom of the upper cup means and internally with respect to each;

(d) means for securing said tubular connecting means in said upper cup means;

(e) a space in said upper cup means defined by said securing means, an internal portion of said cup means and a portion of the tubular connecting means;

(f) port means for providing communication internally of said tubular connecting means and said space;

(g) annular valve means positioned annularly about said tubular connecting means and external of the bottom of said upper cup means;

(h) a highly flexible annular cup means having a cylindrical wall and having a bottom positioned between said annular valve means and the bottom of said upper cup means;

(i) the cylindrical wall positioned to be in normally snug fitting engagement with the lower portion of the outer portion of the upper cup means;

(j) a passgeway between said space through the bottom of said upper cup means whereby excess pressurized gas may be vented out the bottom of the upper cup means between the external bottom thereof and the annular cup and further between the wall of said annular cup and the lower portion of the outer portion of the upper cup means to impart vibrating action to said cylindrical wall of said annular cup means.

2. The gas connector of claim 1 wherein the highly flexible cup means is constructed of thin rubber.

3. The gas connector of claim 2 wherein the lower means and the tubular connecting means is a one piece construction.

4. The gas connector of claim 2 wherein the port means is at least one slot in the tubular connecting means located internally of the upper cup means.

5. The gas connector of claim 4 wherein the annular valve means has a portion about said tubular connecting means and is larger than the opening in the bottom of the upper cup means through which the tubular connecting means occupies and said larger portion is connected together by a narrower cylindrical portion.

6. The gas connector of claim 5 wherein the tubular connecting means is retained in said upper means by an annular cap seal connected thereto.

7. The gas connector of claim 6 wherein the opening in the bottom of the upper cup means has at least one axially disposed slot or hole and defines a portion of the passageway.

* * * * *